United States Patent [19]

Mueller

[11] 4,377,868

[45] Mar. 22, 1983

[54] TOMOGRAPH FOR THE PRODUCTION OF TRANSVERSE LAYER IMAGES

[75] Inventor: Franz Mueller, Moehrendorf, Fed. Rep. of Germany

[73] Assignee: Siemens Aktiengesellschaft, Berlin & Munich, Fed. Rep. of Germany

[21] Appl. No.: 250,060

[22] Filed: Apr. 1, 1981

[30] Foreign Application Priority Data

May 22, 1980 [DE] Fed. Rep. of Germany ....... 3019606

[51] Int. Cl.³ .......................... A61B 6/00; G01T 1/29
[52] U.S. Cl. .................................... 378/019; 378/207
[58] Field of Search ............................. 378/19, 4, 207

[56] References Cited

U.S. PATENT DOCUMENTS 4,138,610 2/1979 Weinkauf .............................. 378/19
4,278,889 7/1981 Erker .................................... 378/19

Primary Examiner—Alfred E. Smith
Assistant Examiner—T. N. Grigsby
Attorney, Agent, or Firm—Hill, Van Santen, Steadman, Chiara & Simpson

[57] ABSTRACT

In an exemplary embodiment, several measuring channels include amplifier circuits subject to zero point drift during measuring signal interruptions. For each measuring channel of the radiation receiver, a register comprising a plurality of memory locations for correction values is present, whose input is connected to the measuring channel output following the amplifier circuit and whose output is connected to the measuring channel input in front of the amplifier circuit. Each register supplies to the associated measuring channel input a correction signal having a value in dependence upon the measuring channel output signal during a preceding signal interruption and such as to correct for any zero point drift of the amplifier circuit.

3 Claims, 2 Drawing Figures

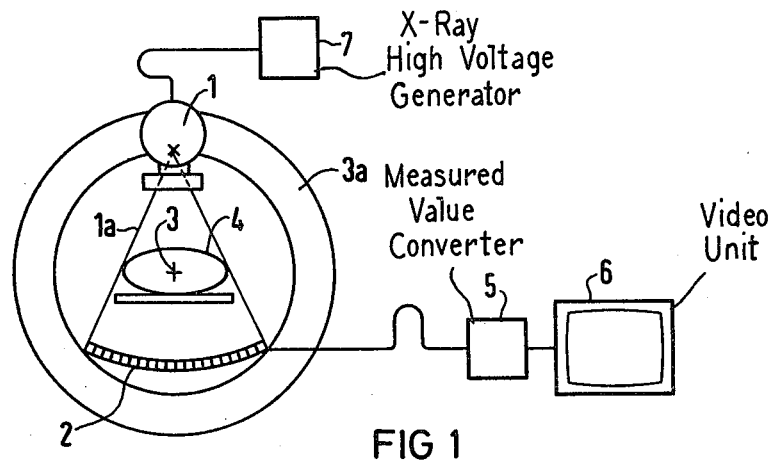
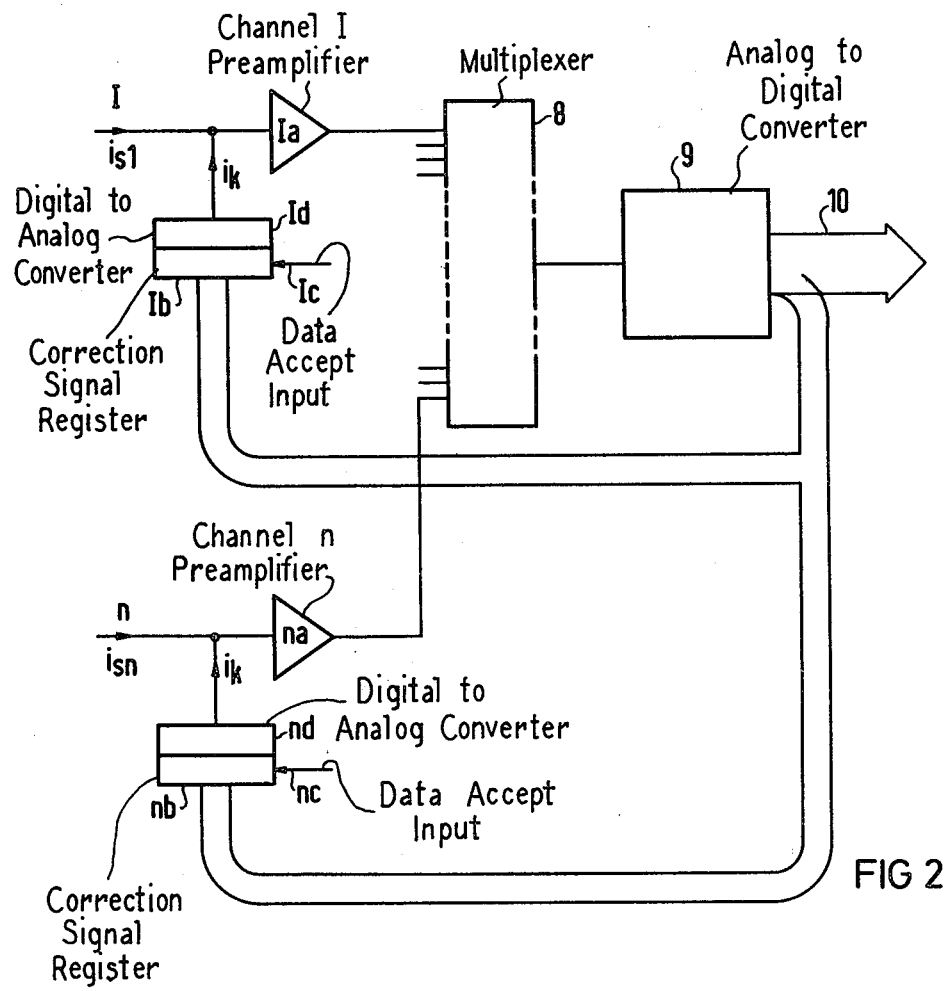

4,377,868

TOMOGRAPH FOR THE PRODUCTION OF TRANSVERSE LAYER IMAGES

BACKGROUND OF THE INVENTION

The invention relates to a tomographic apparatus for the production of transverse layer images of a radiography subject, comprising a radiation measuring arrangement including a radiation source, which generates a radiation beam penetrating the radiography subject and having a cross-sectional extent perpendicular to the layer plane approximately equal to the layer thickness, and a radiation receiver with an array of measuring channels which converts the radiation intensity behind the subject into corresponding electrical signals, comprising a rotating device for the measuring arrangement, and comprising a measurand converter for the transformation of the signals delivered by the radiation receiver into a layer image, wherein, in every measuring channel of the radiation receiver, an individual detector and an amplifier circuit are disposed.

A tomograph of this type is described, for example, in the German OS No. 2,627,433. This tomograph, a so-called computer tomograph, permits the computation of the attenuation values of image points, arranged in a matrix in the examined layer, and the image display of these attenuation values. For every measuring channel it must be taken into consideration here that, in the case of a switched-off x-ray tube; i.e., during the signal interruptions, the measuring channel-output signal can deviate from zero due to zero point drifting occurring in the channel amplifier. This deviation is to be taken into account during the processing of the measuring signals at the channel outputs.

SUMMARY OF THE INVENTION

The object underlying the invention resides in designing a tomograph of the type initially cited such that an automatic detection and compensation of the zero point drifting of the amplifiers in the measuring channels can proceed at regular time intervals.

In accordance with the invention, this object is achieved in that, for every measuring channel of the radiation receiver, a correction value generator; e.g. a register with a plurality of memory locations for correction values, is present, whose input is connected to the measuring channel output after the amplifier circuit, and whose output is connected to the measuring channel input in front of the amplifier circuit, and which supplies to the measuring channel input a correction signal which is selected in dependence upon the measuring channel output signal during signal interruptions, with the aim of controlling the measuring channel output signal to a zero value during the signal interruptions. In the case of the inventive tomograph, in the measuring interruptions, the output signal of each measuring channel is detected and is supplied in the form of an address e.g. to a register in which, among a number of addresses which are dependent upon the desired precision, correction signals for the inputs of the measuring channels are stored. The correction signal corresponding to the signal detected at the channel output can be automatically supplied to the input of the measuring channel, so that the measuring channel output signal corresponds to the measured value with high precision during the subsequent measurement.

The invention shall be explained in greater detail in the following on the basis of an exemplary embodiment illustrated on the accompanying drawing sheet; and other objects, features and advantages will be apparent from this detailed disclosure and from the appended claims.

BRIEF DESCRIPTION OF THE DRAWINGS

FIG. 1 illustrates a tomographic apparatus for the purpose of explaining the inventive idea; and FIG. 2 illustrates the parts of the tomograph according to FIG. 1 which are significant in terms of the invention.

DETAILED DESCRIPTION

In FIG. 1, a tomographic apparatus is illustrated comprising an x-ray tube 1 as the radiation source and a radiation receiver 2, which has on the order of magnitude over one hundred, e.g. 512 individual detectors arranged in an array. The x-ray tube 1 emits a radiation beam $1a$ whose cross-sectional dimension perpendicular to the examined layer plane is equal to the layer thickness and which is of such a dimension in the layer plane that the entire radiography subject is permeated by radiation. The radiation receiver 2 is curved about the focus of the x-ray tube 1. The measuring arrangement 1, 2, with the aid of a rotating frame $3a$, is rotatable about an axis 3, which approximately coincides with the longitudinal axis of the radiography subject 4. The number of detectors of the radiation receiver 2 is selected corresponding to the desired image resolution, so that, on the basis of a rotation of the measuring arrangement 1, 2, the attenuation values of an image point matrix of the irradiated transverse layer of the radiography subject 4 can be computed by a computer of measured value converter 5 and displayed in the form of an image on a video unit 6. The x-ray tube 1 is supplied by an x-ray high voltage generator 7.

Connected to the output of each individual detector of the radiation receiver 2 is a measuring channel which leads to the computer 5. In this measuring channel, amplifier circuits are arranged which can drift in the course of time, so that, in a signal pause, the output signal of such an amplifier circuit can deviate from zero. The measures for compensation of these deviations are explained in greater detail on the basis of FIG. 2.

In FIG. 2, a measuring channel I and a measuring channel n are illustrated. The remaining measuring channels are constructed analogously to these two measuring channels. All measuring channels are coupled via preamplifiers $1a$ through $na$, to a multiplexer 8 which successively supplies the output signals of the preamplifiers to an analog-to-digital converter 9. The digital output signals of the analog-to-digital converter 9 are supplied via a data bus to the computer 5. They are branched off from the data bus 10 and supplied in parallel fashion to digital memory registers Ib through nb in the measuring channels I through n. In the registers Ib through nb, a number of correction signals is stored in memory locations, of which one in each instance is called up corresponding to the respective input signal; i.e., corresponding to the output signal of the analog-to-digital converter 9. When a signal interruption occurs, then a data accept signal is supplied to the registers Ib through nb at the inputs Ic through nc, so that the correction signal corresponding to the input signal is supplied to a digital-to-analog converter Id through nd connected respectively to the output of the registers Ib through nb. The resulting analog output signal corrects the input signal, which corresponds to the measured radiation intensity, such that, in a signal interruption the channel output signal on the data bus 10 for each measuring channel is zero.

Thus, in the registers Ib through nb, a correction table is stored corresponding to the correction signal required for each output signal of a measuring channel in the case of a zero input signal, the values of said correction table being called up by the measuring channel output signals in the signal interruptions and utilized for the purpose of zero point correction. The correction can here proceed very rapidly. The bit-depth of the digital-to-analog converters Id through nd conforms to the error to be maximally corrected.

It is conceivable within the framework of the invention to replace the registers Ib through nb by counters and to activate the latter by a digital comparator which interprets the output data of the analog-to-digital converter 9 in such a fashion that, when these data are zero during signal interruptions, the counter reading is not altered; i.e., clock-pulses are not forwarded to the counter, but that, when the output of the analog-to-digital converter 9 is less than zero during signal interruptions, the counter is controlled for upward-counting, and that, in the case in which the output is greater than zero, it is controlled for downward counting. In dependence upon the respective counter reading, a correction current is then supplied to the input of the respective amplifier Ia through na via a digital-to-analog converter.

The null value at the output of the analog-to-digital converter 9 during the signal interruptions can be the value zero, but also it can be another, random, but defined value. In the latter instance, in utilizing a counter for the activation of the respective preamplifier Ia through na, the significant feature is that the comparator controlling the counter effects no alteration of the counter reading when the defined value is present during signal interruptions, and that, in the other instance, it effects an upward counting, or downward counting, respectively.

It will be apparent that many modifications and variations may be effected without departing from the scope of the novel concepts and teachings of the present invention.

I claim as my invention:

1. Tomographic apparatus for the production of transverse layer images of a radiography subject, comprising a radiation measuring arrangement including a radiation source for generating a radiation beam penetrating the radiography subject, whose cross-sectional extent perpendicular to the layer plane is approximately equal to the layer thickness, and a radiation receiver with an array of measuring channels for converting the radiation intensity behind the subject into corresponding electrical signals, comprising a rotating device for the measuring arrangement, and comprising a measured value converter for the transformation of the signals delivered by the radiation receiver into a layer image, each measuring channel of the radiation receiver including an individual detector of the radiation receiver and an amplifier circuit, and having a measuring channel input connected with the individual detector for receiving a measured value signal to be processed, and a measuring channel output connected with the amplifier circuit for supplying measured value output signals during measurement cycles and being operative to supply further output signals during measurement signal interruptions, each measuring channel (I through n) of the radiation receiver (2) having correction value generator means (Ib through nb) with an input connected to the measuring channel output following the amplifier circuit (Ia through na), and having an output connected to the measuring channel input in front of the amplifier circuit (Ia through na), and means comprising said correction value generator means for generating a correction signal which is a function of any deviation of a further output signal at each measuring channel output from a predetermined null output value during a measurement signal interruption, said correction signal generator means being operative for supplying the correction signal so generated to the corresponding measuring channel input during a subsequent measurement cycle for correcting the resulting measured value output signal supplied at the measuring channel output, characterized in that the correction value generator means comprises a register (Ib through nb) with a plurality of memory locations for supplying respective correction values.

2. Tomographic apparatus according to claim 1, characterized in that, between the measuring channel output and the register (Ib through nb) an analog-to-digital converter (9) is disposed, and that, between the register (Ib through nb) and the measuring channel input, a digital-to-analog converter (Id through nd) is disposed, and that the register (Ib through nb) is a digital memory register.

3. Tomographic apparatus according to claim 1, characterized in that the register (Ib through nb) has a control input (Ic through nc) for receiving a data acceptance signal during measurement signal interruptions.

* * * * *